(12) United States Patent
al-Soufi et al.

(10) Patent No.: US 7,268,268 B2
(45) Date of Patent: Sep. 11, 2007

(54) DIMERIZATION OF OLEFINS

(75) Inventors: Farouk al-Soufi, Riyadh (SA); Sami A. I. Barri, Riyadh (SA); Yajnavalkya Subrai Bhat, Riyadh (SA); Altaf Husain, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 198 days.

(21) Appl. No.: 10/312,704

(22) PCT Filed: Apr. 19, 2001

(86) PCT No.: PCT/EP01/04431

§ 371 (c)(1), (2), (4) Date: Jun. 30, 2003

(87) PCT Pub. No.: WO02/06191

PCT Pub. Date: Jan. 24, 2002

(65) Prior Publication Data

US 2004/0030212 A1 Feb. 12, 2004

(30) Foreign Application Priority Data

Jun. 26, 2000 (EP) .................................. 00113486

(51) Int. Cl.
*C07C 2/04* (2006.01)
*C07C 2/24* (2006.01)

(52) U.S. Cl. ...................... 585/510; 585/514

(58) Field of Classification Search ................ 585/510, 585/514

See application file for complete search history.

(56) References Cited

U.S. PATENT DOCUMENTS

| 3,760,026 | A |   | 9/1973 | Reusser et al. |
|-----------|---|---|--------|----------------|
| 5,118,900 | A |   | 6/1992 | Drake |
| 5,434,328 | A | * | 7/1995 | Barri et al. .................. 585/666 |
| 5,672,800 | A | * | 9/1997 | Mathys et al. ............. 585/520 |
| 5,866,096 | A | * | 2/1999 | Verduijn et al. ............ 423/702 |

FOREIGN PATENT DOCUMENTS

| EP | 0124998 | 11/1984 |
|----|---------|---------|
| EP | 0 247 802 A | 12/1987 |
| WO | WO 91 18851 A | 12/1991 |

* cited by examiner

*Primary Examiner*—Glenn Caldarola
*Assistant Examiner*—In Suk Bullock
(74) *Attorney, Agent, or Firm*—William J. Spatz; Jim Wheelington

(57) ABSTRACT

A process for the dimerization of at least one olefin with a carbon number between 2 and 10 by contacting the feed with a catalyst system comprising at least: (a) tectometallosilicate zeolite with having TON-type structure, (b) tectometallosilicate zeolite with having MTT-type structure, (c) tectometallosilicate zeolite with the same structure as that of the ZSM-48 zeolite, or (d) silicoaluminophosphate (SAPO) zeo-type with AEL-type structure; under dimerization condition to produce highly branched olefins.

13 Claims, No Drawings

DIMERIZATION OF OLEFINS

BACKGROUND OF INVENTION

1. Field of the Invention

This invention relates to the conversion of butenes especially isobutene by dimerization to highly branched octenes especially trimethylpentenes and dimethylhexenes, in the presence of a catalyst. This invention also pertains to the use of specific zeolite and/or zeo-type containing catalyst.

Trimethylpentenes are highly valuable intermediates for the production of isooctane by hydrogenation. In addition, both the trimethylpentenes and dimethylhexenes may be used as intermediate for the production of xylenes especially p-xylene. Isooctane and p-xylene are valuable chemicals for gasoline blending and the manufacture of polyester fiber respectively.

2. Description of the Prior Art

Dimerization of butenes especially isobutene is a commercially important reaction. Many catalysts have been claimed for this reaction. For example supported and promoted sulfuric acid and phosphoric acid, and a variety of other catalysts have been claimed in U.S. Pat. Nos. 3,760, 026. 5,118,900 describes the dimerization of isobutene over zeolite Y or a modified zeolite Y. However, these catalysts also produce oligomers of isobutenes. European Patent 0 247 802 describes the isomerization of olefins especially butenes to produce isobutenes over uni-directional medium pore zeolites whereas European Patent 0 124 998 describes the production of transport fuel from small olefins by oligomerization, cracking, and isomerization over medium pore zeolites.

SUMMARY OF THE INVENTION

The present invention relates to the dimerization of butenes especially isobutene over a zeolite or a zeo-type containing catalyst.

DESCRIPTION OF PREFERRED EMBODIMENTS

The present invention relates to the dimerization of butenes especially isobutene over a zeolite or a zeo-type containing catalyst. More specifically, the zeolite or zeo-type material is chosen from any of the following or a combination thereof: (a) tectometallosilicate with having TON-type structure, (b) tectometallosilicate with having MTT-type structure, (c) tectometallosilicate with the same structure as that of the ZSM-48 zeolite, or (d) silicoaluminophosphate (SAPO) with AEL-type structure. These structure types are described in (a) the Atlas of Zeolite Structure Types by W. M. Meier, D. H. Olson and C h. Baerlocher, fourth revised edition (1996), published on behalf of the Structure Commission of the International Zeolite Association, and/or (b) (Handbook of Molecular Sieves, by Rosemarie Szostak (1992), published by van Nostrand Reinhold.

Zeolites and zeotype materials (such as silicoaluminophosphates) are structurally ordered porous materials having a rigid regular three dimensional network of $SiO_4$ and $AlO_4$ tetrahedra in case of the zeolite materials and $SiO_4$, $AlO_4$, and $PO_4$ tetrahedra in the case of silicoaluminophosphates. The tetrahedra are cross-linked by sharing the oxygen atoms forming a structure that is sufficiently open to accommodate voids and/or channels that are capable of sorbing water and hydrocarbons depending on the diameter of the window controlling the entrance to the channel system relative to the size of sorbate species. This has led to zeolites and other zeo-type materials being called "molecular sieves".

The relative population of the different tetrahedral atoms in the framework determines the composition of the framework. The extra-framework material together with the framework composition adds up to the bulk composition of the molecular sieve. Zeolites and zeo-type materials are best classified by their framework topological structure irrespective of their composition, exact cell parameters, or symmetry. A code consisting of three capital letters has been adopted for each known structure type following the recommendations by IUPAC on zeolite nomenclature (Chemical Nomenclature, and Formulation of Composition, of Synthetic and Natural Zeolites).

These nomenclatures refer only to those zeolite and zeo-type materials that have known zeolite. Materials with unknown structure (topology) are referred to by their individual reference but still identified by their x-ray powder diffraction pattern. In addition to their diffraction pattern the structural properties of these zeolite may also be characterized by e.g. their sorption and ion-exchange properties.

The zeolites and zeo-type materials of interest to the invention are those that have a medium pore and unidirectional channel system. Medium pore means that the window controlling the entrance to the channel system consists of 10-T ring, i.e. the window is formed by joining 10 tetrahedra through their oxygen atoms. Unidirectional medium pore channel system means that the channel that is controlled by 10-T-ring window is not intersected by a another channel with another 10-T-ring channel or larger. Examples of the zeolites of interest to this invention include TON-type structure (Theta-1, ZSM-22, NU-10, KZ-2, ISI-1, and their compositional variants), MTT-type structure (ZSM-23, EU-13, KZ-1, IST-4, and their compositional variants), FER-type structure (FU-9, NU-23, ZSM-35, and their compositional variants), ZSM-48 and its compositional variants, AEL-type structure (SAPO-1 I and its compositional variants). All these materials have unidirectional I 0-T-ring channel system as defined above.

These zeolites and zeo-type materials have been found to be effective catalysts for the dimerization of butenes. In particular these catalysts have been found to be effective for the dimerization of isobutene. Although, the known sorption properties of these catalysts indicate that they would not promote the formation of highly branched products such as 2,4,4-trimethylpentene-1 and 2,4,4-trimethylpentene-2, upon the application of these catalysts high conversion and selectivity to the formation of the highly branched products were obtained. Without wishing to affect the novelty of the invention, it seems that the catalytic sites near the pore mouth and on the outside surface of the catalyst crystallites take part in the conversion of the present invention.

Accordingly, the present invention is a process for the dimerization of butenes especially isobutene, said process comprising bringing butenes containing feedstock in the fluid phase into contact with a catalyst containing a zeolite or a zeo-type material in its un-modified, modified, or partially modified H-form characterized in that the zeolite in its H-form has the following composition in terms of the mole ratios of the oxides:

$$(0.9 \pm 0.1)H_{(4-m)}:XO_2:xSiO_2:yH_2O$$

wherein H is a proton, X is one or more of the metals selected from Al, Ga, Zn, Fe, Cr, and B, m is the valency of the metal X in the metal oxide $XO_2$, x is at least 10, y/x is from 0 to 5. In case of using zeo-type materials of AEL-type structure the composition of the H-form is:

$(0-a)H:(Si_aAl_bP_c)O_2:yH_2O$ wherein H is a proton and a, b, and c represent the mole fraction of silicon, aluminium and phosphorous respectively present in a tetrahedral oxides.

When an organic base is used in the synthesis of the zeolite or zeo-type material it is customary that this is removed by calcination in air at a temperature of at 200-600° C., preferably at 300-550° C. When the zeolite or the zeo-type material is synthesized in the absence of organic base the calcination step may not be necessary.

The $H_2O$ content "y" of the zeolite or the zeo-type material is the water of hydration and will depend, within the ratios set above, upon the conditions under which it is dried or calcined and the relative humidity. The $H_2O$ content "y" does not include water which may be notionally presents when the cation is hydrogen. Beside hydrogen other cations such as ammonium, alkali metal, alkaline earth metal, aluminium, or a mixture thereof, may be present in the zeolite or the zeo-type material. The cations present may be replaced partially or wholly by conventional ion exchange treatment. The cation in the catalytically active form is essentially a proton but residual amount of other cations may also be present. The proton or H-form may be prepared by ammonium exchange followed by calcination as mentioned above or by ion exchange with a mineral acid or a combination thereof.

The metal X in the metal oxide $XO_2$ of the zeolite is preferably Al, Ga, Zn, B, or a mixture thereof. The molar ratio of silica to metal X is preferably 10:1 to 200:1.

The molar ratio of the aluminium to phosphorous ratio (b:c) is preferably 0.8:1 to 1.3:1; whereas the molar silicon to aluminium ratio (a:b) is preferably 0.005:1 to 0.4:1. In addition, the aluminium in the composition may be replaced partly or wholly by Ga, B, Fe, or a mixture thereof.

It is well known to those skilled in the art that the x-ray powder diffraction pattern, in terms of the relative intensities ($I/I_0 \times 100$) or the interplanar spacing (d), may vary. The variation usually depends on many factors. Examples of these factors include the degree of hydration, the skeletal composition, the type of the cations present in the material, the presence of occluded organic or inorganic materials, the presence of preferred orientation, the aspect ratio of the crystallites or their average size and distribution, the experimental errors involved in the measurement, or the techniques used with regard to the arrangement of slit (i.e. fixed slits vs. auto-divergent slits) in the measurement. Taking these variables into consideration and from studying the x-powder diffraction pattern as a whole, the structure-types of a given material can be identified.

The zeolite material is suitably synthesized by mixing a source of silica, a source of metal X, a source of alkali metal(s), water and an organic or inorganic nitrogen containing base to form a homogeneously mixed gel and crystallizing the gel at a temperature above 70° C. under the self generated pressure. In case of the zeo-type material, it is suitably synthesized by mixing a source of aluminium or its substituent, a source of phosphorous, a source of silica, water, and an organic nitrogen containing base to form a homogenously mixed gel and crystallizing the gel at a temperature above 70° C. under the self generated pressure. The zeolite or the zeo-type materials of the present invention may be bound in a suitable binding material using methods and binding materials well known in the art. Examples of binders that may be suitably used include silica, alumina, aluminophosphates, clays such as kaolin and meta-kaolin, or a combination thereof. The bound catalyst may be subjected to further activation treatment which may be hydrothermally which includes steaming at elevated temperature, thermochemically which include heating the catalyst in a reducing or oxidative environment such as passing a flow of oxygen, air or hydrogen. The catalyst may be activated by carrying out any or more of the above treatments either consecutively or con-currently. These treatments may be carried out before the introduction of the hydrocarbon feed or/and periodically after catalytic cycles of times on stream with the hydrocarbon feed. The reactor may be a batch reactor or a flow reactor with a fixed bed catalyst. However other systems for example fluidized bed system may also be used.

The dimerization reaction can be carried out by contacting the dimerizable olefins with the catalysts. Whereas the catalyst will be present in the solid phase the feedstock and the products may be present in the liquid or the gas phase depending on the structure and molecular weight of the individual compounds and the reaction conditions used. The feedstock may contain the olefins with number of the carbon number varies from 2 to 10, with butenes are the preferred feedstock with isobutene is the most preferred feedstock. The hydrocarbon feed may contain a diluent such as an alkane, nitrogen, water, . . . etc. The most preferred alkane diluents are pentane, hexane, heptane, or octane. The isobutene feedstock may also contain re-cycled isobutene and triisobutenes and other by-products.

The applied temperature of the dimerization reaction and the temperature of the catalyst can vary depending on the catalyst used, the content of the feedstock, whether the feed contains a diluent, and the type of the reactor used. Typically a temperature range of 0° C. and 300° C. is suitable. A temperature range of 10° C. to 150° C. is most preferred. The applied pressure will depend on many factors such as the catalyst performance and the engineering aspect of the process e.g. liquid phase vs. gas phase and optimization of cost. The reactor pressure can be equal or higher than atmospheric pressure in order to optimize the yield and the selectivity of the desired products such as isooctenes (2,4,4 trimethylpentene-1 and 2,4,4 trimethylpentene-2). A pressure range of 15 psig to 1000 psig is preferred and 30 psig to 200 psig is most preferred.

The weight hourly space velocity (WHSV) defines the rate of the introduction of the feed for a given catalyst charge and it has an influence on the performance of the catalyst and the productivity rate of the desired products. WHSV is defined as the weight of the reactants per hour fed per weight of the catalyst. Thus it has a unit of $h^{-1}$. In the present invention a WHSV of higher than 0.1 $h^{-1}$ may be employed. A WHSV range of 0.5 $h^{-1}$ to 100 $h^{-1}$ is preferred with 1.0 $h^{-1}$ to 30 $h^{-1}$ is most preferred.

The desired products are highly branched olefins specifically octenes. These product may be hydrogenated to produce high octane alkylate for gasoline blending or aromatized into xylenes for the production of polyester.

The present invention will be further demonstrated by specific examples.

EXAMPLE 0.80 grains of sodium hydroxide and 1.10 of sodium aluminate (ex. BDH and containing 40% by weight $Al_2O_3$ and 28% by weight $Na_2O$) were dissolved in 20 grams of distilled water. 50 grams of ammonia solution containing 25% by weight of $NH_3$ were added while stirring followed by 50 grams of ludox AS40 (colloidal silica containing 40% by weight silica). The ludox was added slowly over ten minutes period while stirring ensuring that the hydrogel formed is always homogeneous. The hydrogel was stirred for a further 10 minutes and then loaded into a 150 ml PTFE lined pressure vessel. The pressure vessels were rotated in an oven at 150° C. for 36 hours. It is known to those are skilled in the art that zeolites are metastable and the optimum period of crystallization depend on factors affecting the effective rate of formation of the desired zeolite and may vary depending on for example the equipment used and the degree and type of stirring.

After the crystallization period the solid was filtered, washed several times with distilled water, and dried at 90° C. The dried solid was examined by X-ray powder diffraction and found to be consistent with the TON-type structure with some cristoblite material present. The X-ray powder diffraction pattern is shown in Table 1. Chemical analysis showed that the powder had a Si/Al molar ratio of 34.7.

The zeolite powder was stirred in excess ammonium nitrate solution (concentration ~1 mole/liter and using ~50 ml of solution per gram of zeolite) for a few hours. The powder was filtered and a fresh ammonium nitrate solution was added and the treatment was repeated once more. The filtered zeolite was finally washed copiously with distilled water and dried at 90° C.

The zeolite powder was packed into a 2.5 cm diameter die and pressed at a pressure of about 8 metric tons for 2 minute. The formed tablet was broken down into granules and sieved between 1 and 2 mm sieves.

30 cm$^3$ were packed into the middle of a tubular stainless steel reactor (1.0 mm inner diameter and 45 cm length) and sandwiched between two of at least 20 cm$^3$ of inert beads. The reactor had a coaxial tube (0.2 cm outer diameter) to enable the measuring of the catalyst bed temperature via an inserted thermocouple. The reactor was re-connected into the micro-reactor and a 50 cm$^3$/minute-air flow was passed over the catalyst and the temperature was raised to 550° C. at the rate of 60° C./hour. The temperature was maintained for at least 8 hours and then reduced to the required reaction temperature. The catalyst was then flushed with a nitrogen flow to remove traces of air. Isobutene feed was introduced via a liquid pump from a reservoir maintained at room temperature and pressure of 170 psig to keep the isobutene in the liquid state.

The results of the dimerization reaction are shown in Table 2. The products C$_8$=were isomers of octenes with highly branched skeletons. The main portion of the isomers were 2,4,4-trimethyl-pentene-2,2,4,4-trimethyl-pentene-1,3, 4,4-trimethyl-pentene-2,2-methyl-heptene-3,1-ethyl-1-methylcyclopentane, and 2,3,4-trimethyl-pentene-2. The products C$_{12}$=also consisted of highly branched isomers.

The example has been provided merely to illustrate the practice of invention and should no be read as to limit the scope of the invention or the appended claims in any way.

TABLE 1

| 2-θ (degrees) | d-spacing (Angstroms) | Relatively Intesity 100 × I/I$_0$ |
|---|---|---|
| 8.128 | 10.896 | 59.6 |
| 10.123 | 8.731 | 22.1 |
| 12.751 | 6.937 | 27.5 |
| 16.322 | 5.426 | 14.6 |
| 18.334 | 4.835 | 4.2 |
| 19.387 | 4.575 | 13.5 |
| 20.318 | 4.367 | 100.0 |

TABLE 1-continued

| 2-θ (degrees) | d-spacing (Angstroms) | Relatively Intesity 100 × I/I$_0$ |
|---|---|---|
| 21.667 | 4.098 | 28.9 |
| 24.179 | 3.678 | 78.9 |
| 24.592 | 3.617 | 52.9 |
| 25.696 | 3.464 | 36.8 |
| 26.653 | 3.342 | 11.0 |
| 26.993 | 3.300 | 9.2 |
| 27.714 | 3.216 | 5.6 |
| 30.002 | 2.976 | 4.7 |
| 30.403 | 2.938 | 6.4 |
| 30.742 | 2.906 | 6.2 |
| 32.131 | 2.783 | 4.4 |
| 32.745 | 2.733 | 5.2 |
| 32.975 | 2.714 | 5.1 |
| 35.591 | 2.520 | 21.7 |
| 35.935 | 2.497 | 7.9 |
| 36.862 | 2.436 | 11.1 |
| 37.991 | 2.366 | 7.7 |
| 43.715 | 2.069 | 5.1 |
| 44.433 | 2.037 | 5.5 |
| 45.282 | 2.001 | 4.9 |
| 47.734 | 1.904 | 4.9 |
| 48.565 | 1.873 | 9.6 |

TABLE 2

Feed: Isobutene
Catalyst: SAB-9CNC-TON-type structure
WHSV: 5 h$^{-1}$

| Hours on Stream | Temperature ° C. Furnace/Catalyst | Reactor Pressure psig | Conversion Wt % | Selectivities Wt % | | |
|---|---|---|---|---|---|---|
| | | | | C1-C3 | C8= | C12= |
| 1.0 | 150/195 | Ambient | 38.1 | 0.54 | 82.8 | 3.9 |
| 2.0 | 45/155 | 50-100* | 98.4 | nd | 72.3 | 26.2 |
| 6.0 | 45/155 | 50-100* | 83.7 | nd | 53.5 | 46.5 |

*pressure could not be maintained high enough in the absence of the initial nitrogen pressure due to fast condensation of the products.

The invention claim is:

1. A process for dimerizing a feed consisting essentially of isobutene, comprising contacting the feed under dimerization conditions at temperatures from 10° C. to 150° C. and with a catalyst system which comprises at lease one of a: (a) tectometallosilicate zeolite having TON-type structure, (b) tectometallosilicate zeolite having MTT-type structure, (c) tectometallosilicate zeolite having ZSM-48 type structure, or (d) silicoaluminophosphate zeo-type material with AEL-type structure; wherein the zeolite and the zeo-type material are wholly in the H-form, and the zeolite has the following composition and mole ratios:

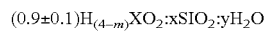
$(0.9\pm0.1)H_{(4-m)}XO_2:xSiO_2:yH_2O$ wherein H is a proton, X is one or more of Al, Ga, Zn, Fe, Cr, and B, m is the valency of X in XO$_2$, x is at least 10, y/x is from 0 to 5; and the zeo-type material has the following composition and mole ratios:

$(O-a)H:(Si_aAl_bP_c)O_2:yH_2O$ wherein H is a proton, a, b, and c represent the number of atoms of silicon, aluminum and phosphorus respectively present in the zeo-type material and y is moles of hydration water in the zeo-type material.

2. The process according to claim 1, wherein the catalyst system is activated by heating in steam.

3. The process according to claim 1, wherein the feed contains inert diluent.

4. The process according to claim 3, wherein the diluent is a hydrocarbon.

5. The process according to claim 4, wherein said contacting is carried out at a pressure ranging from 15 psig to 1000 psig.

6. The process according to claim 5, wherein said contacting is carried out at a pressure ranging from 30 psig to 200 psig.

7. The process according to claim 5, wherein said contacting is at WHSV of 0.5 $h^{-1}$ to 100 $h^{-1}$.

8. The process according to claim 6, wherein said contacting is at WHSV of 1.0 $h^{-1}$ to 30 $h^{-1}$.

9. The process according to claim 8, wherein the catalyst system is activated by heating in steam.

10. The process according to claim 9, wherein the feed contains an inert diluent.

11. The process according to claim 10, wherein said diluent is octane.

12. The process according to claim 10, wherein said feed is contacted with said catalyst system at a pressure ranging from 15 psig to 1000 psig.

13. The process according to claim 12, wherein said contacting is at WHSV of 1.0 $h^{-1}$ to 30 $h^{-1}$.

* * * * *